United States Patent
Dar et al.

(10) Patent No.: US 7,146,220 B2
(45) Date of Patent: *Dec. 5, 2006

(54) DEVICE FOR MUSCLE STIMULATION

(75) Inventors: Amit Dar, Ra'anana (IL); Roger Nathan, Ra'anana (IL)

(73) Assignee: N.E.S.S. Neuromuscular Electrical Stimulation Systems Ltd., Ra'anana (IL)

( * ) Notice: Subject to any disclaimer, the term of this patent is extended or adjusted under 35 U.S.C. 154(b) by 102 days.

This patent is subject to a terminal disclaimer.

(21) Appl. No.: 10/491,236

(22) PCT Filed: Sep. 30, 2002

(86) PCT No.: PCT/IL02/00797

§ 371 (c)(1),
(2), (4) Date: Mar. 29, 2004

(87) PCT Pub. No.: WO03/030803

PCT Pub. Date: Apr. 17, 2003

(65) Prior Publication Data

US 2004/0236384 A1    Nov. 25, 2004

(30) Foreign Application Priority Data

Sep. 30, 2001  (IL) .................................. 145718

(51) Int. Cl.
*A61N 1/18* (2006.01)
(52) U.S. Cl. ......................................... 607/48; 607/149
(58) Field of Classification Search .................. 607/48, 607/49, 50, 51, 149
See application file for complete search history.

(56) References Cited

U.S. PATENT DOCUMENTS

| 1,422,396 | A | * | 7/1922 | Wappler | ...................... 607/149 |
| 1,644,803 | A | * | 10/1927 | Wappler | ...................... 607/149 |
| 4,558,704 | A |   | 12/1985 | Petrofsky | |
| 4,580,569 | A |   | 4/1986 | Petrofsky | |
| 5,330,516 | A |   | 7/1994 | Nathan | |
| 5,562,707 | A |   | 10/1996 | Prochazka et al. | |
| 6,829,510 | B1 | * | 12/2004 | Nathan et al. | ............... 607/149 |

* cited by examiner

*Primary Examiner*—Jeffrey R. Jastrzab
(74) *Attorney, Agent, or Firm*—Mark M. Friedman

(57) ABSTRACT

A device for muscle stimulation, including: two exoskeletal shells, each including an outer member including an at least semi-rigid material, the shells being configured to at least partly, surround a limb portion of a user, and kinematic connection means connecting the shells and providing the shells with at least one degree of freedom in translation, so as to enable the shells to move in a substantially linear movement with respect to each other.

35 Claims, 14 Drawing Sheets

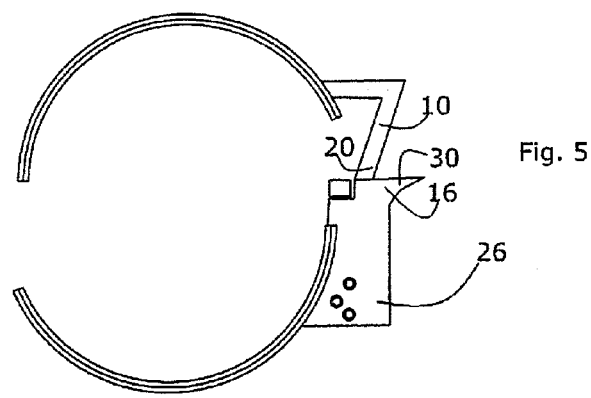
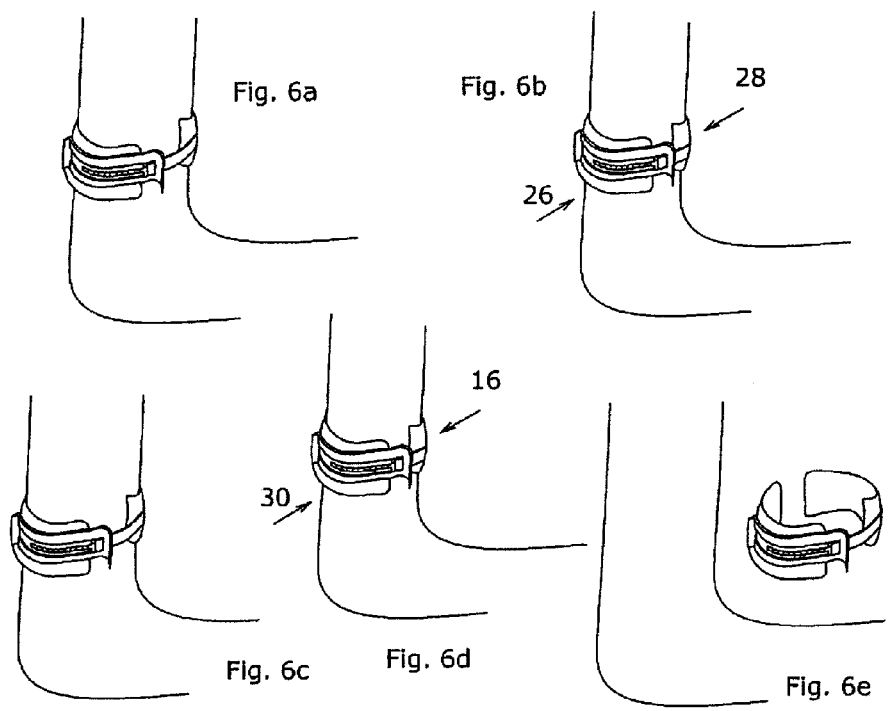

DEVICE FOR MUSCLE STIMULATION

FIELD AND BACKGROUND OF THE INVENTION

The present invention relates to a surface neuroprosthetic device for muscle stimulation.

Movement impairment in a limb can result from a number of neurological or orthopedic pathological conditions. Activation of selected muscles of the limb by functional electrical stimulation (FES) to generate controlled movements has been used, both as a therapeutic modality and for the improvement or restoration of activities of daily living (ADL) or functional restoration.

Devices based on surface electrical stimulation which have been developed for activating specific body sites include the dropfoot system, which activates the ankle joint, modifying hemiplegic gait; hybrid FES-orthosis systems for restoring gait in spinal cord-injured patients, and systems for therapeutic activation and functional restoration of the hand, such as the Handmaster, described in U.S. Pat. No. 5,330,516 (Nathan). Other prior art devices are described in U.S. Pat. No. 5,562,707 (Prochazka); U.S. Pat. Nos. 4,580,569 and 4,558,704 (both to Petrofsky). Use of these devices requires them to be placed on the body limb and to be removed, possibly once or several times, each day. One of the main barriers to widespread use of surface neuroprostheses has been the lengthy time and high level of expertise required to position the electrode array and to hold the electrodes on the limb surface. This is generally carried out by the patient himself, who suffers from neurological or orthopedic deficits. A hemiplegic patient, having the use of only one hand, will often be required to don and doff the neuroprosthesis by himself. Quadriplegic users may be able to don or doff the neuroprosthesis, or may require assistance.

The soft tissue of the paralyzed or plegic limb is highly flexible and mobile. Mechanical interaction between the limb and the device during the donning of the neuroprosthesis can result in geometric distortion of the limb's soft tissue. This problem should be addressed, as neuroprostheses are intended to be worn for several hours each day.

SUMMARY OF THE INVENTION

It is therefore one of the objects of the present invention to provide a neuroprosthetic device that can be easily donned and doffed by a hemiplegic user without distortion of the soft tissue of the limb.

A further object of the present invention is to provide a neuroprosthetic device containing an array of surface electrodes, whereby a hemiplegic user of the device can position the entire electrode array accurately and repeatably on to his own limb, with facility.

Another object of the present invention is to provide a neuroprosthetic device that effectively serves as a supporting structure for the surface electrode array, so as to enable the array to interact mechanically in a desirable manner with the soft tissue of the plegic or paralyzed limb, particularly during device donning.

It is a further object of the present invention for the above-described mechanical interaction to be controlled solely by the contralateral hand of the patient.

Finally, it an object of the present invention to provide a neuroprosthetic device that enables the complex donning procedure to be carried out not only by a single contralateral hand, but in a single motion.

Hence, according to the teachings of the present invention, there is provided a device for muscle stimulation, including: two exoskeletal shells, each including an outer member including an at least semi-rigid material, the shells being configured to at least partly surround a limb portion of a user, and kinematic connection means connecting the shells and providing the shells with at least one degree of freedom in translation, so as to enable the shells to move in a substantially linear movement with respect to each other.

According to another aspect of the present invention there is provided a device for muscle stimulation, including: two exoskeletal shells, each including an outer member including an at least semi-rigid material, the shells being configured to at least partly surround a limb portion of a user, and kinematic connection means connecting the shells and providing the shells with an arcuate movement relative to each other.

According to yet another aspect of the present invention there is provided a method including the steps of: providing a device including: (i) two exoskeletal shells, each including an outer member including an at least semi-rigid material, the shells being configured to at least partly surround a limb portion of a user, and (ii) kinematic connection means connecting the shells and providing the shells with at least one degree of freedom in translation, and moving the shells in a substantially linear movement with respect to each other for opening and closing the device.

According to further features in the described preferred embodiments, the kinematic connection means also provide the shells with one degree of freedom in rotation.

According to still further features in the described preferred embodiments, the device further includes retaining means for retaining the shells in a selected position of translation.

According to still further features in the described preferred embodiments, the retaining means is a pawl and ratchet arrangement, the pawl being associated with a first of the shells and the ratchet being associated with a second of the shells.

According to still further features in the described preferred embodiments, the device further includes at least one tension spring connected at one end to a first of the shells and at an opposite end to a second of the shells so as to produce tension between the shells, the tension urging the shells into a normally-closed position.

According to still further features in the described preferred embodiments, the device further includes at least one compression spring connected at one end to a first of the shells and at an opposite end to a second of the shells so as to produce tension between the shells, the tension urging the shells into a normally-open position.

According to still further features in the described preferred embodiments, the ratchet is an integral part of a flexible strip operatively connected to a slider.

According to still further features in the described preferred embodiments, the substantially linear movement is effected by a pin riding in an inclined slot in a slider connected to one of the shells and kinematically connected to a trigger member of the pawl, whereby a sliding movement of the trigger member causes the slider to move in a direction perpendicular to the sliding movement.

According to still further features in the described preferred embodiments, opening and closing movements of the shells are effected by an interaction of a first pair of inclined planes fixedly attached to a first of the shells with a second pair of inclined planes fixedly attached to a second of the shells, wherein the second pair of inclined planes is biased by a force of a tension spring to facilitate the closing movement of the shells.

According to still further features in the described preferred embodiments, the device is designed and configured to be donned using a single hand.

According to still further features in the described preferred embodiments, the device further includes at least one cushion, each cushion operatively connected to a shell and disposed between the shell and the limb portion.

According to still further features in the described preferred embodiments, the device further includes at least one surface electrode, each surface electrode operatively connected to a shell and disposed between the shell and the limb portion, the shell designed and configured to provide a pressure to the electrode, so as to maintain electrical contact between the electrode and a skin surface of the limb portion.

According to still further features in the described preferred embodiments, the substantially linear movement of the shells allows for maintaining a natural limb shape of the limb portion.

According to still further features in the described preferred embodiments, the kinematic connection means include a cantilever.

According to still further features in the described preferred embodiments, the cantilever is connected to each of the shells at a single connection joint.

According to still further features in the described preferred embodiments, the kinematic connection means include a cantilever.

According to still further features in the described preferred embodiments, the cantilever is connected to the shells such that the pressure delivered to the electrode is a substantially even pressure.

According to still further features in the described preferred embodiments, the device further includes a spring biasing mechanism, operatively connected to a shell and to the cantilever, the spring mechanism for biasing a pressure exerted on a skin surface of the limb portion.

According to still further features in the described preferred embodiments, the device further includes a spring biasing mechanism operatively connected to a shell and to the cantilever, the spring mechanism for biasing a pressure exerted on the at least one surface electrode.

According to still further features in the described preferred embodiments, the at least one surface electrode includes a first electrode and a second electrode, and wherein the spring mechanism is for biasing a pressure exerted on the first electrode with respect to the second electrode.

According to still further features in the described preferred embodiments, the device further includes a locking mechanism operatively connected to a shell and to the cantilever, the locking mechanism for locking a connection joint in a fixed position.

According to still further features in the described preferred embodiments, the locking mechanism includes an adjustable screw assembly for adjustably locking the connection joint in a fixed position.

According to still further features in the described preferred embodiments, the cantilever includes circumferential adjustment means for circumferentially fitting the device to the limb portion of the user.

According to still further features in the described preferred embodiments, the cantilever includes longitudinal adjustment means for longitudinally fitting the device to the limb portion of the user.

According to still further features in the described preferred embodiments, the cantilever includes radial adjustment means for radially adjusting the device to the limb portion of the user, so as to adjust a gap width between the cantilever and a shell.

According to still further features in the described preferred embodiments, the cantilever includes a displacement mechanism between the cantilever and a shell, for providing a localized, positive deformation of the shell, enabling control of local pressure applied to the limb portion.

According to still further features in the described preferred embodiments, the shell further includes a second material having a greater flexibility with respect to the at least semi-rigid material, the second material for enabling local, controlled flexibility of the shell.

According to still further features in the described preferred embodiments, the second material is an elastomer.

According to still further features in the described preferred embodiments, the device further includes retaining means for retaining the shells in a selected position along the arcuate movement.

According to still further features in the described preferred embodiments, the opening and closing is performed with a single hand.

According to still further features in the described preferred embodiments, the method further includes the step of donning the device with a single hand.

According to still further features in the described preferred embodiments, the method further includes the step of donning the device with a single hand.

According to still further features in the described preferred embodiments, the method further includes the step of donning the device in an accurate and repeatable manner.

According to still further features in the described preferred embodiments, the method further includes the step of donning the device while maintaining a natural shape of the limb portion.

It will be appreciated that the principles underlying the device according to the present invention do not limit its usefulness to a specific limb. Thus, with minor changes in shape and size, necessitated by the different geometries of different limbs, the present device is suitable to use with the upper arm, the leg, and the thigh as well.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 5 represents the embodiment of FIG. 3, in which angular spreading open movement has been added to the linear spreading open movement;

FIGS. 6a–6e represent the various stages in the donning and doffing of the device according to the present invention:

FIG. 22 is a custom-shaped shell for use in conjunction with the modular neuroprosthetic device of FIG. 15.

DESCRIPTION OF THE PREFERRED EMBODIMENTS

Figure 1:
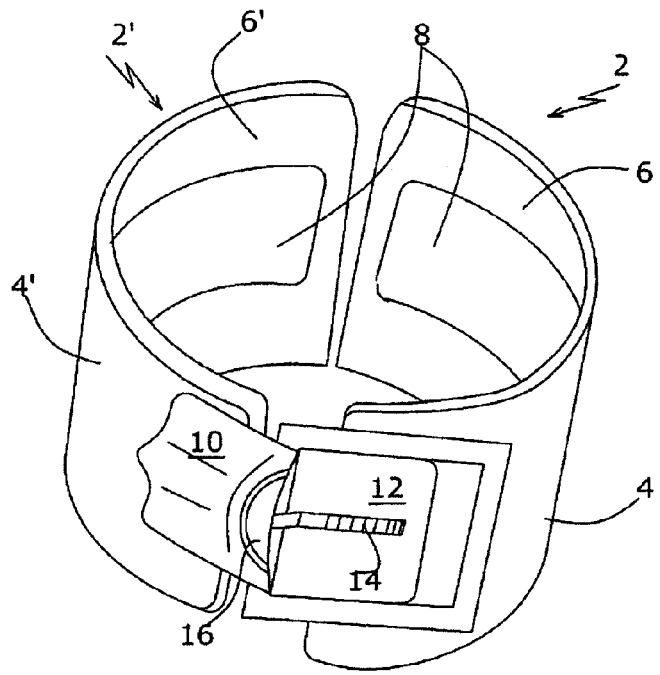
FIG. 1 is a perspective view of a first embodiment of the device according to the present invention, in its closed limit state.

The present invention is a surface neuroprosthetic device for muscle stimulation.

The principles and operation of the surface neuroprosthetic device of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Referring now to the drawings, there is shown in FIG. 1 a first embodiment of the device according to the present invention. The device is shown in one of its limit states, in which the split-sleeve-like structure is fully closed. The device, as illustrated, is intended to be worn on the upper arm, as shown in FIG. 6c. Seen are an anterior shell 2 and a posterior shell 2', consisting of at least semi-rigid outer members 4, 4' and elastically yielding, back-up or cushion members 6, 6'. The two shells 2, 2' and their cushions 6, 6' substantially envelop the entire circumference of the upper arm segment at the approximate center of the length of the arm, at the midpoint of the biceps muscle. The interior of shells 2, 2', when mounted on the arm, has a substantially barrel-like shape, which reflects the geometry of the upper arm. Also shown are electrodes 8, each shell 2, 2' being provided with two electrodes, by way of example.

A characterizing feature of the device of the present invention is the kinematic connection between shells 2, 2', which is achieved by means of a mechanism that facilitates:

donning of the device;

closing of the device, to the point where proper contact with the muscles is achieved with minimal distortion of the soft tissue of the limb;

locking of the device in this state, and reopening of the device for eventual doffing.

This mechanism described in greater detail further below, provides shells 2, 2' with one degree of freedom in translation, permitting the linear distance between the shells to be increased or decreased. The mechanism also provides one degree of freedom in rotation, whereby, at the end of a limited translational movement, an angular, swiveling movement is provided between shells 2, 2' permitting the device to spread open to a sufficient degree to allow it to be placed on, or removed from a limb, e.g. an upper arm of the user.

As used herein in the Specification and in the claims section that follows, the term "maintaining natural limb shape" and the like refer to a device-donning or device-wearing action that is performed without undue distortion of the soft tissue of the limb, so is to enable the device to be donned accurately and repeatably, and so as to avoid pinching discomfort and impairment of blood flow associated with distortion of the soft tissue.

Figure 2:
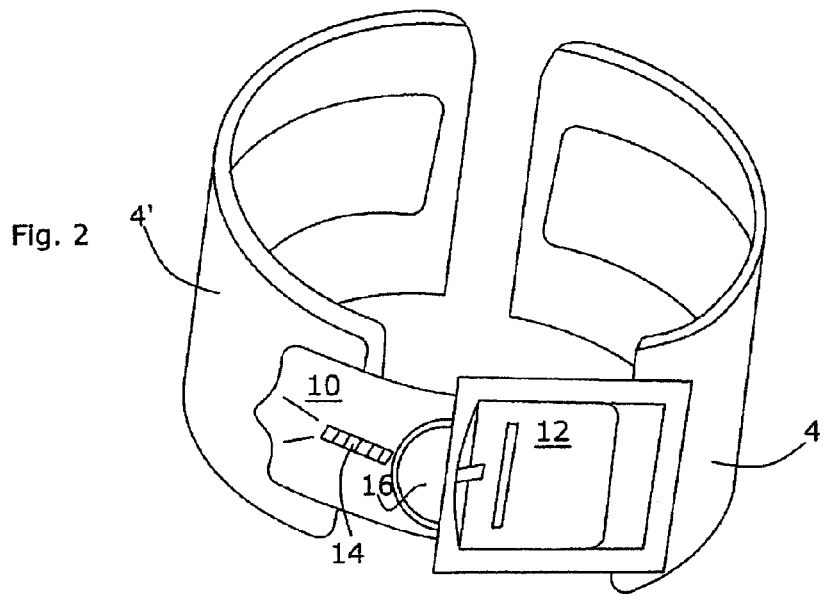
FIG. 2 is a perspective view of the device of FIG. 1 at the end of its linear spreading open movement.

The above-mentioned mechanism consists of a pawl-and-ratchet arrangement, including a slider 10 integral with posterior shell 2', moving within a guide member 12 and carrying a ratchet 14, as seen in FIGS. 1 and 2, the latter representing the embodiment of FIG. 1 in the fully spread-open state.

Seen in both FIGS. 1 and 2, as part of the anterior shell 4, is pawl release trigger 16, the pressing of which is the first step in removal or doffing of the device.

Figure 3:
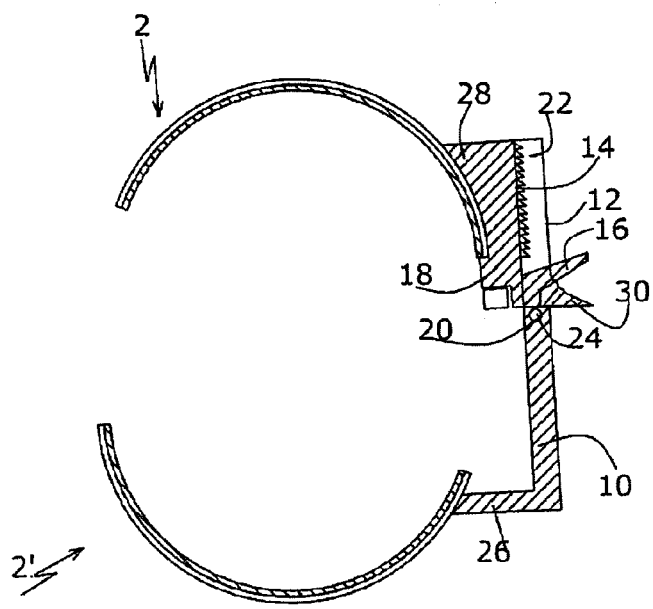
FIG. 3 is a cross-sectional top view of a variant of the embodiments of FIGS. 1 and 2 at the end of its linear spreading open movement.

A full view of the mechanism is afforded by FIG. 3, which illustrates a cross-sectional view of a second embodiment of the device in which ratchet 14 is an integral part of guide member 12 and is shown at the end of the linear movement thereof. Shown are slider 10, guide member 12, ratchet 14, release trigger 16 and pawl 18. The trigger 16/pawl 18 unit is hingedly articulated to slider 10 by means of a pivot 20, and is spring-biased towards the position in which pawl 18 engages the saw teeth of ratchet 14.

Figure 4:
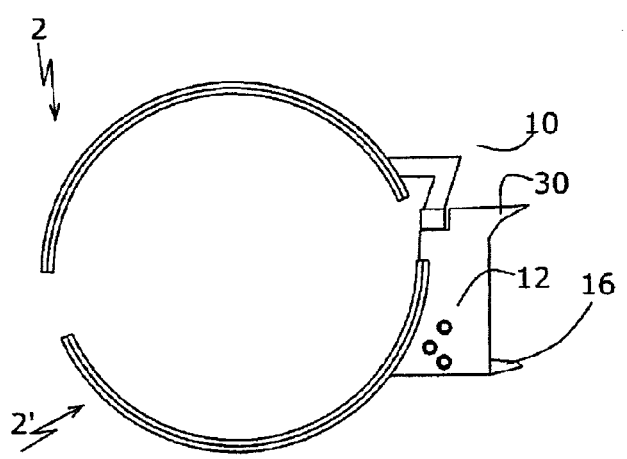
FIG. 4 is a top view of the embodiment of FIG. 3, in the fully closed position.

To open the device for donning from its extreme limit of closure illustrated in FIG. 4, the thumb and index finger of the user are applied against pawl trigger 16 and counterhold 30, respectively, so as to disengage pawl 18 from ratchet 14 and push slider 10 out of guide member 12. At the end of the linear stroke, slide member 10 leaves guiding groove 22 (FIG. 3), at which instant, torsion spring 24 causes the now-free slider 10 to swivel up to about 20°, resulting in the shells 2, 2' assuming a second, totally spread-open position, as shown in FIG. 5.

The donning- and doffing procedures are summarized in the following, as illustrated in FIGS. 6a–6e:

Donning

The present invention is intended to enable such a complex procedure as donning a multi-channel neuroprosthesis to be carried out not only with one hand, but in a single motion. After having been fully opened in the above-described manner, the device is held in a contralateral hand of the user by the handles 26 and 28 and brought around in front of the chest and slipped over the upper arm (FIG. 6a), and is closed around the arm by applying the thumb and index finger of the contralateral hand (or by an attendant) against handling surfaces 26, 28, respectively (FIGS. 3 and 6b). Pawl 18 slides over the slanting flanks of the saw-teeth of ratchet 14 and eventually engages an undercut flank of the ratchet, thereby locking the device in the final donned position shown in FIG. 6c. The right arm of the user is shown, with the ratchet mechanism located on the outside of the arm.

A motion limiter, e.g., an adjustable stop, is preferably provided along slider 10 to prevent the user from closing the device too tightly on his arm.

Doffing

Doffing (FIG. 6d) begins with the thumb and index finger being applied against pawl trigger 16 and counterhold 30, respectively (FIG. 4), disengaging pawl 16 from ratchet 14 and pushing out slider 10 from guide member 12, which results in the swiveling open of shells 2, 2'. The device is then pulled off the arm, as shown in FIG. 6e.

Surfaces and components 14, 16, 18, 26, 28 and 30 are shown to best effect in FIGS. 3 and 4.

Figure 7:
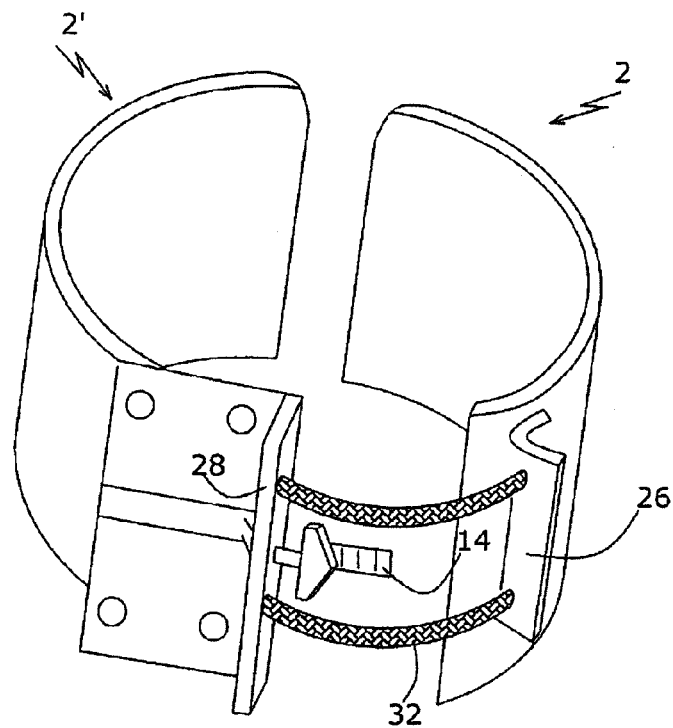
FIGS. 7, 7a illustrate a further embodiment of the invention in the open and closed positions, respectively.

FIG. 7 illustrates another embodiment of the device of the present invention in a fully open position. This embodiment is provided with linear movement only; however, this linear movement is sufficiently large to facilitate lateral access to the upper arm.

Figure 7A:
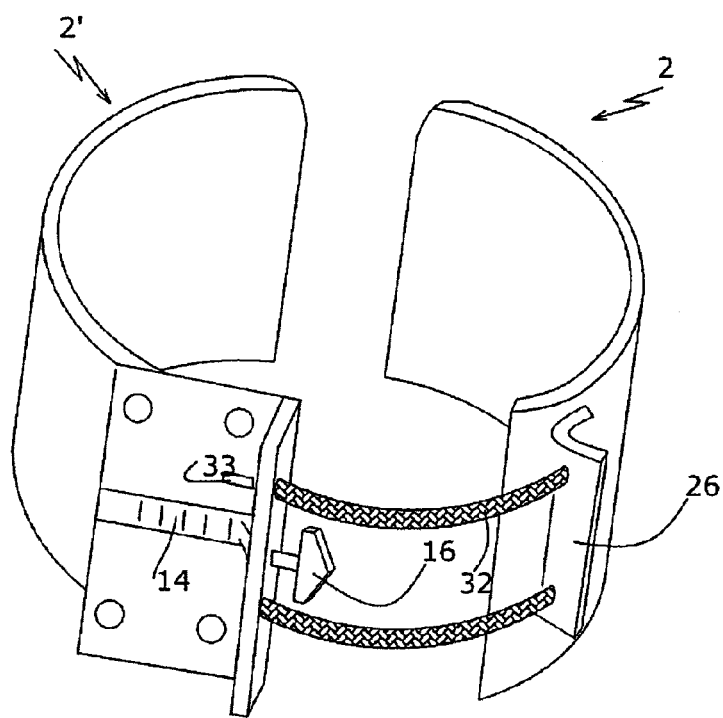

Further seen in FIG. 7 are two helical springs 32 on guide rods 33 (see FIG. 7a). Springs 32 can be tension springs, in which case, the springs close the device on to the limb.

The numerals in some of the following figures indicate components that are functionally equivalent to corresponding components of previously discussed embodiments.

Figure 8:
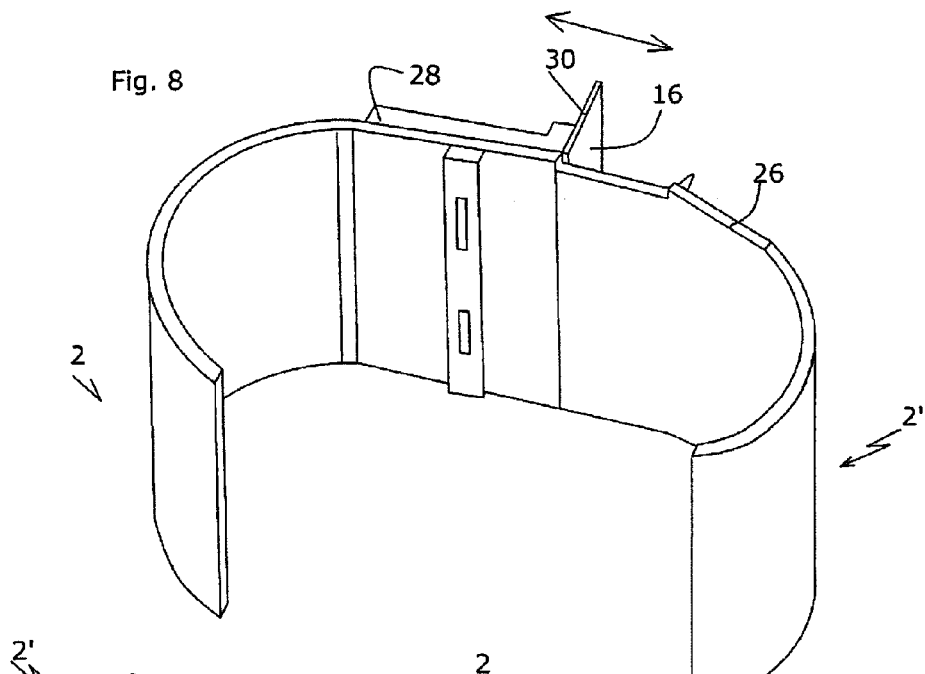
FIG. 8 depicts another embodiment of the invention, having only linear movement.

FIG. 8 illustrates another embodiment of the device, in which the opening and closing movement of the shells is solely linear and must therefore be extensive enough to facilitate introduction of the limb without the assistance of the above-discussed swivel movement.

Figure 9:
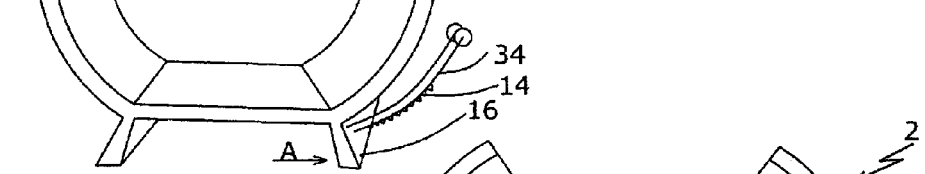
FIG. 9 depicts a further embodiment in which the ratchet is an integral part of a flexible strip.
Figure 10:
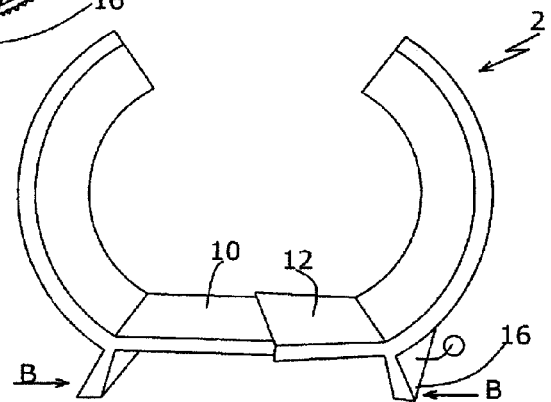
FIG. 10 shows the device of FIG. 9 in the open position.

FIGS. 9 and 10 represent yet another embodiment of the device in which ratchet 14 is an integral part of a flexible strip 34, flexible strip 34 being attached at one end to a slider 10 that moves within guide member 12. For opening, pressure is applied in the direction of either of arrows A.

FIG. 10 shows the device of FIG. 9 in the open position. To close the device, pressure is applied in the direction of arrows B.

Figure 11:
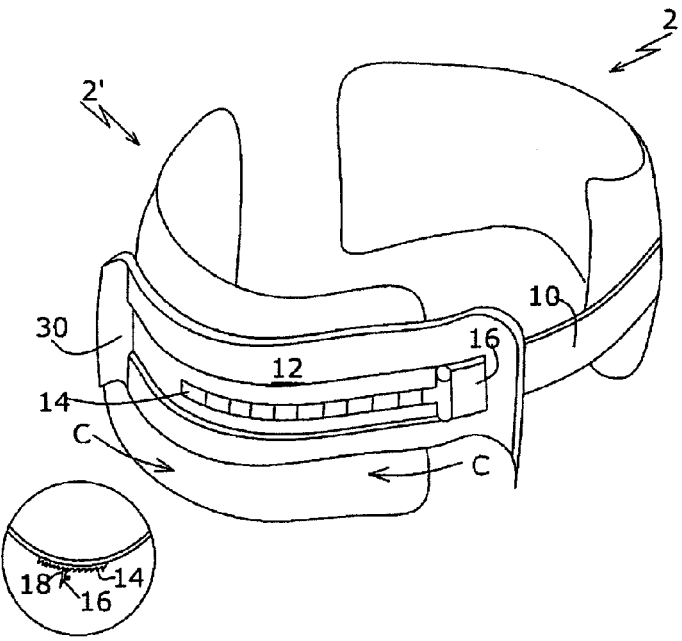
FIG. 11 illustrates yet another embodiment of the device.
Figure 12:
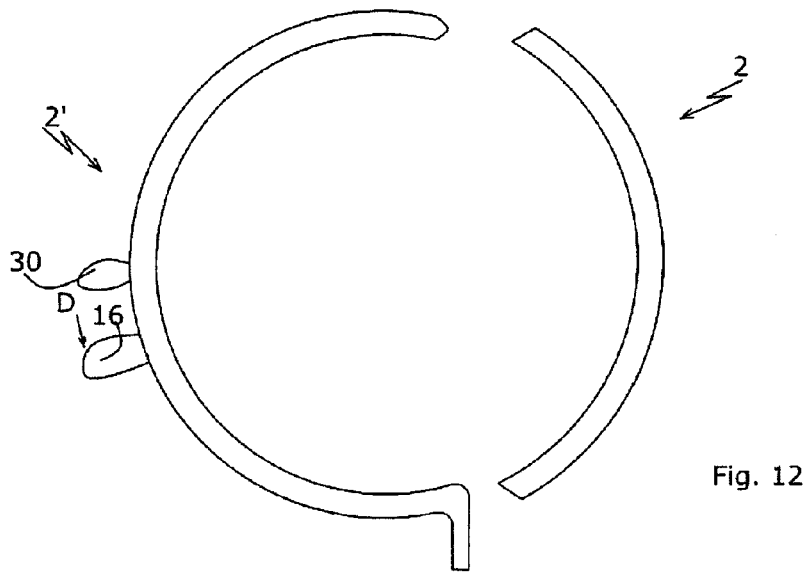
FIG. 12 shows the embodiment of FIG. 11 in the closed state.

FIG. 11 illustrates an embodiment of the device having an arcuate movement, in which ratchet 14 is part of, or fixedly attached to, shell 2'. Elastic slider 10, fixedly attached to shell 2, carries pawl trigger 16 at the free end thereof. Guide member 12 is fixedly attached to shell 2'. To close the device, pressure is applied in the direction of arrows C. The closed state of the embodiment of FIG. 11 is shown in FIG. 12. To open the device, pressure is applied in the direction of arrows D.

Figure 13:
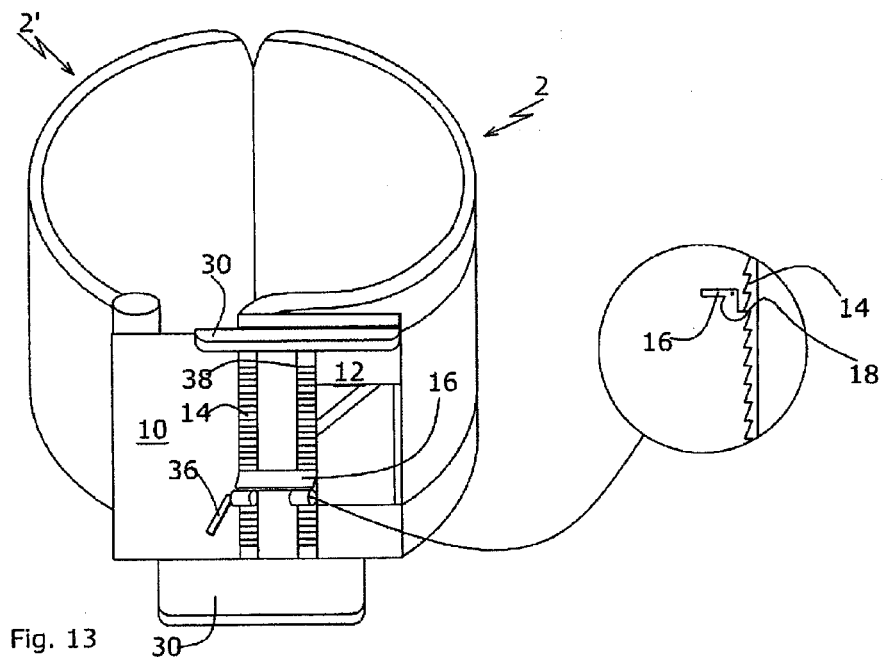
FIG. 13 illustrates an embodiment of the invention which uses an inclined-plane opening and closing mechanism.

FIG. 13 illustrates another locking and shell shifting mechanism, which uses the inclined-plane principle for the linear opening and closing movements of the shells. Fixedly attached to shell 2' is a slider 10, provided with an inclined slot 36. Slider 10 moves within guide member 12, which is fixedly attached to shell 2. Mounted on guide member 12 is a double ratchet 14, divided by a slot 38. A pin (not shown), mounted on spring-loaded pawl trigger 16, projects through slot 38 and engages inclined slot 36. Applying pressure on pawl trigger 16 in the direction towards upper counterhold 30 disengages panel 18 and causes the pin to ride up in slot 36, thereby causing the device to open. Applying force on trigger 16 in the direction towards lower counterhold 30' allows pawl 18 to slide over the inclined ratchet teeth flanks and causes the pin to ride down in slot 36, thus causing the device to close.

Figure 14:
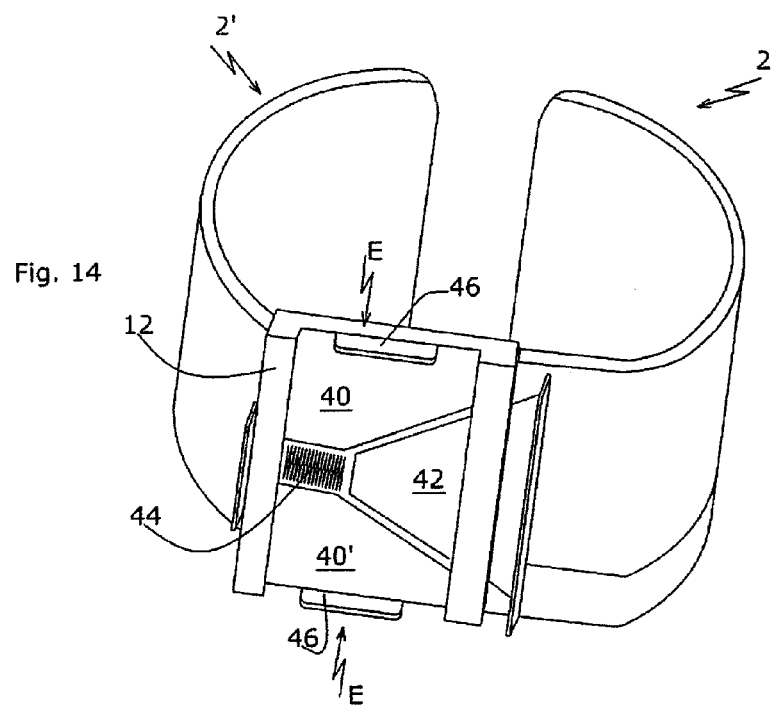
FIG. 14 represents another embodiment of an inclined-plane opening and closing mechanism, using a double inclined plane.

A further inclined-plane mechanism is illustrated in FIG. 14. This embodiment is a double-plane arrangement, with one pair of inclined planes 40, 40' being slidable within a guide member 12 fixedly attached to shell 2', and counter-planes 42, 42' fixedly attached to shell 2, which in turn are also slidable within guide member 12 and are urged by tension spring 44 towards the closed position, making the device a normally-closed device. Pressure applied on surfaces 46, in the direction of arrows E, will cause the inclined edges of planes 40 to engage with the edges of counter-plane 42, thus opening the device.

The above-described donning and doffing procedures, illustrated in FIGS. 6a–6e, and referring to the upper arm of a user, also apply analogously to devices designed for use with, for example, the leg or the thigh.

While in the upper arm device discussed as a specific example of the applicability of the present invention to different limbs, shells 4 were arranged one opposite the other at the same height, the shells of a leg device are advantageously arranged with an axial offset relative to one another, to conform to the geometry of the limb.

Figure 15:
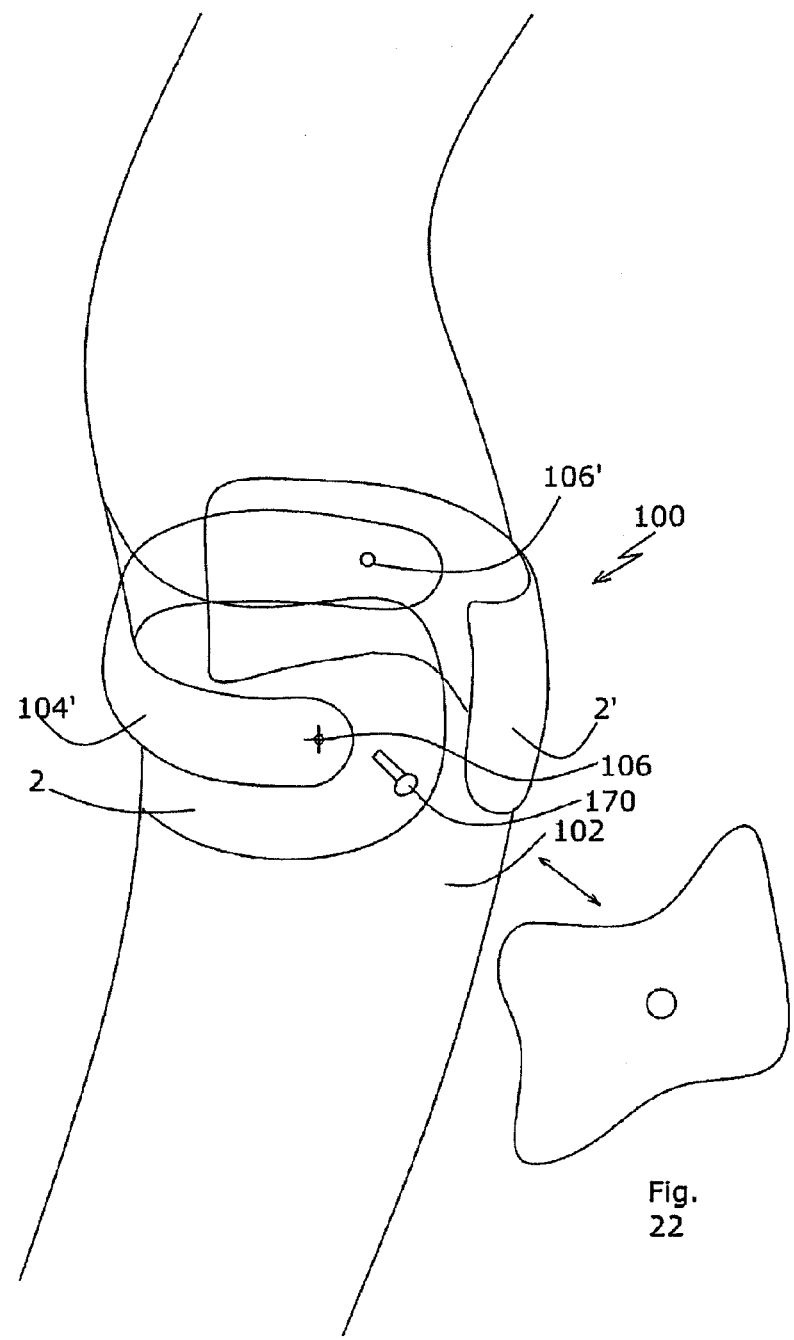
FIG. 15 is a schematic illustration of another preferred embodiment of the neuroprosthethic device of the present invention, in which the shells are connected by a horseshoe-shaped cantilever.
Figure 16:
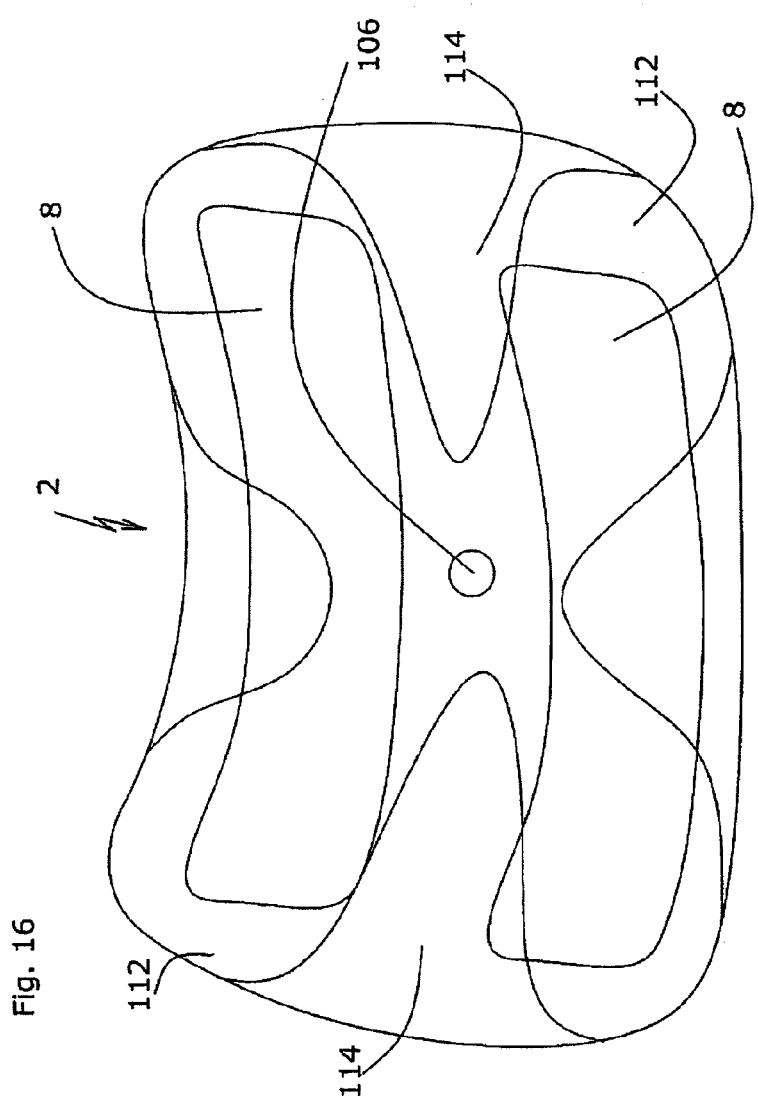
FIG. 16 is a schematic illustration of a shell for a neuroprosthetic device of the present invention, the shell having a composite structure including at least two materials of varying rigidity.

FIG. 15 is a schematic illustration of another preferred embodiment of the neuroprosthetic device of the present invention. Neuroprosthetic device 100, disposed on limb segment 102, includes shells 2, 2' connected by a horseshoe-shaped cantilever 104. Cantilever 104 is attached to each shell 2, 2' by a single connection joint 106, 106', preferably disposed in a substantially central area of each shell 2, 2'. Together shells 2, 2' substantially enclose limb segment 102. In addition to connecting shells 2, 2', cantilever 104 applies forces on to shells 2, 2', which, in turn, apply upon limb segment 102 the requisite forces and force interactions during the use of neuroprosthetic device 100. The mechanical properties of shells 2, 2', cantilever 104, and each connection joint 106 connecting therebetween, are designed so as to optimize the quality of interaction between the neuroprosthesis and limb segment 102, which determines the quality of activation of limb segment 102. Optional displacement mechanism 170 is described hereinbelow.

Figure 17:
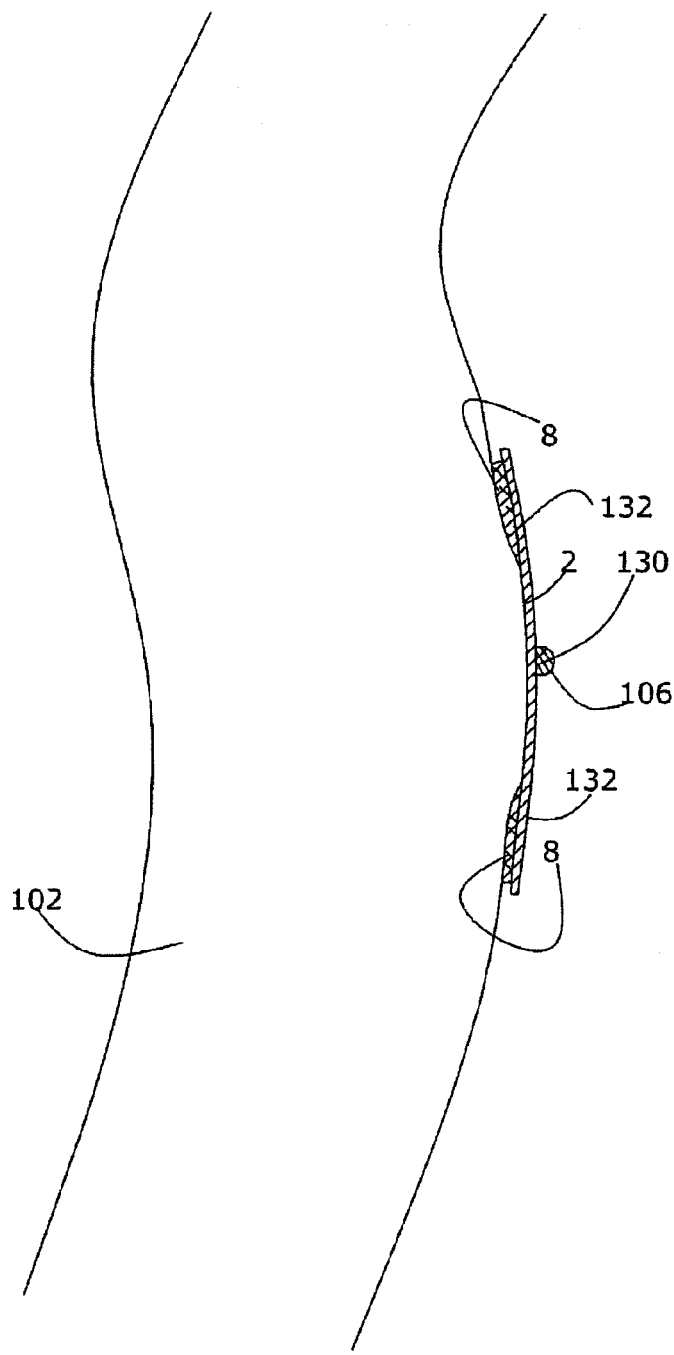
FIG. 17 is a partial cross-sectional view of a neuroprosthetic device contacting a limb segment, in which a point force is applied to a geometrical center of the shell.
Figure 18:
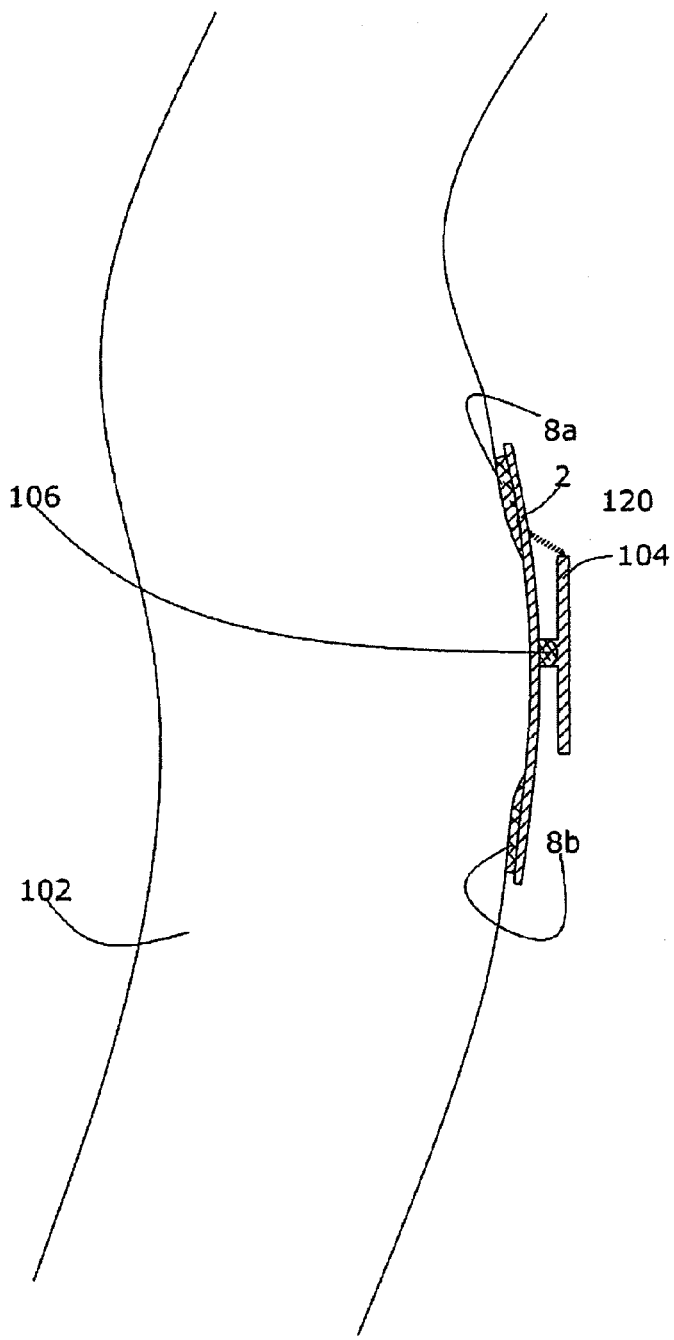
FIG. 18 retains the view of the neuroprosthetic device of FIG. 17, and includes a cantilever and an additional mechanical constraint imposed between the cantilever and shell.
Figure 19:
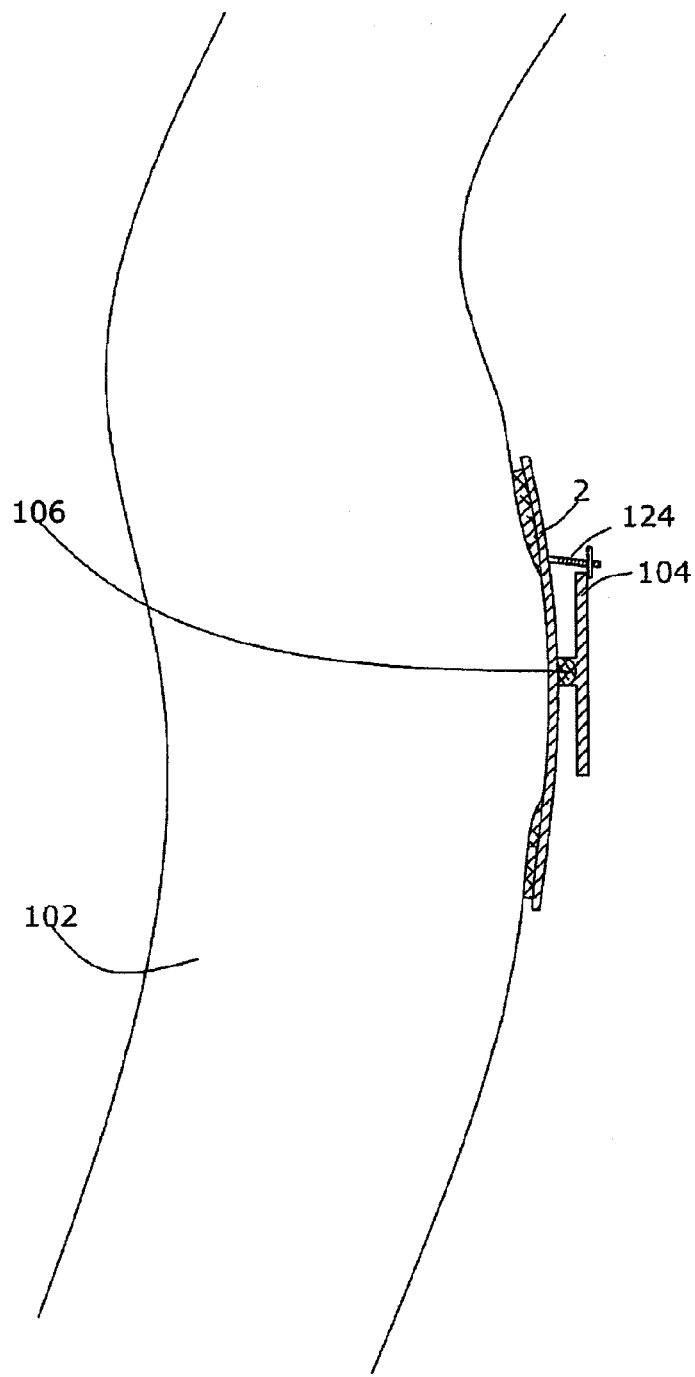
FIG. 19 retains the view of the neuroprosthetic device of FIG. 17, and includes a cantilever and a locking mechanism for locking connection joint 106 in a fixed position.

Schematic views of several preferred embodiments are provided in FIGS. 17–19. FIG. 17 shows a partial, cross-sectional view of a neuroprosthetic device contacting limb segment 102. Disposed between a surface of limb segment 102 and shell 2 are surface electrodes 8. The pressure distribution between shell 2 and the body segment surface depends on the force vector applied by the cantilever (not shown) to the shell. Application of a point force to a geometrical center 130 of shell 2 results in a self-balancing system. The electrode pressure will distribute itself in a substantially balanced and even distribution on to the limb surface.

FIG. 18 shows the view of the neuroprosthetic device of FIG. 17, with cantilever 104, and with the addition of an additional mechanical constraint, e.g. spring mechanism 120. The additional moment at connection joint 106, provided by a compression spring mechanism 120, tends to bias the pressure on surface electrodes 8a, 8b. Consequently, a higher pressure is applied to surface electrode 8b with respect to surface electrode 8a.

FIG. 19 shows the view of the neuroprosthetic device of FIG. 17, with cantilever 104, and with an adjustment and locking mechanism for adjusting connection joint 106, and for locking connection joint 106 in a fixed position. The particular adjustment/locking mechanism shown by way of example in FIG. 19 is screw assembly 124. Screw assembly 124 cancels any self-adjusting capability of the shell orientation, such that shell 2 is essentially a rigid extension of cantilever 104. Consequently, after adjusting the orientation of shell 2 according to the needs of an individual patient, screw assembly 124 causes shell 2 to be fixed in orientation. Typically, the orientation of shell 2 should be adjusted by a clinician for an individual device user during the initial device fitting session.

It should be emphasized that shells 2, 2', in addition to applying the surface electrodes (e.g. surface electrodes 8, 8' shown in FIG. 1 or surface electrodes 8 shown in FIGS. 16-19) to the surface of limb segment 102, interact mechanically with the tissue of limb segment 102.

Although the body limb surface is static at rest, on activating a neuroprosthesis, limb segment articulations and muscle contractions cause changes in the limb segment profile. An element of flexibility in the shells may allow the shell to better preserve intimate contact with the skin surface. One means of achieving this flexibility, while preserving the ability of the shell to transfer significant electrode pressure to the limb surface is provided schematically in a shell 2 of FIG. 16. Shell 2 has a composite structure including an at least semi-rigid material 112 (e.g., semi-rigid plastic) and a more flexible material 114 (e.g., an elastomer). Flexible material 114 allows for controlled shell flexibility in certain regions and directions, while semi-rigid material 112 gives structural support to shell 2 and allows force application in other directions. Preferably, connection joint 106 and electrodes 8 are disposed in regions of semi-rigid material 112.

Figure 20:
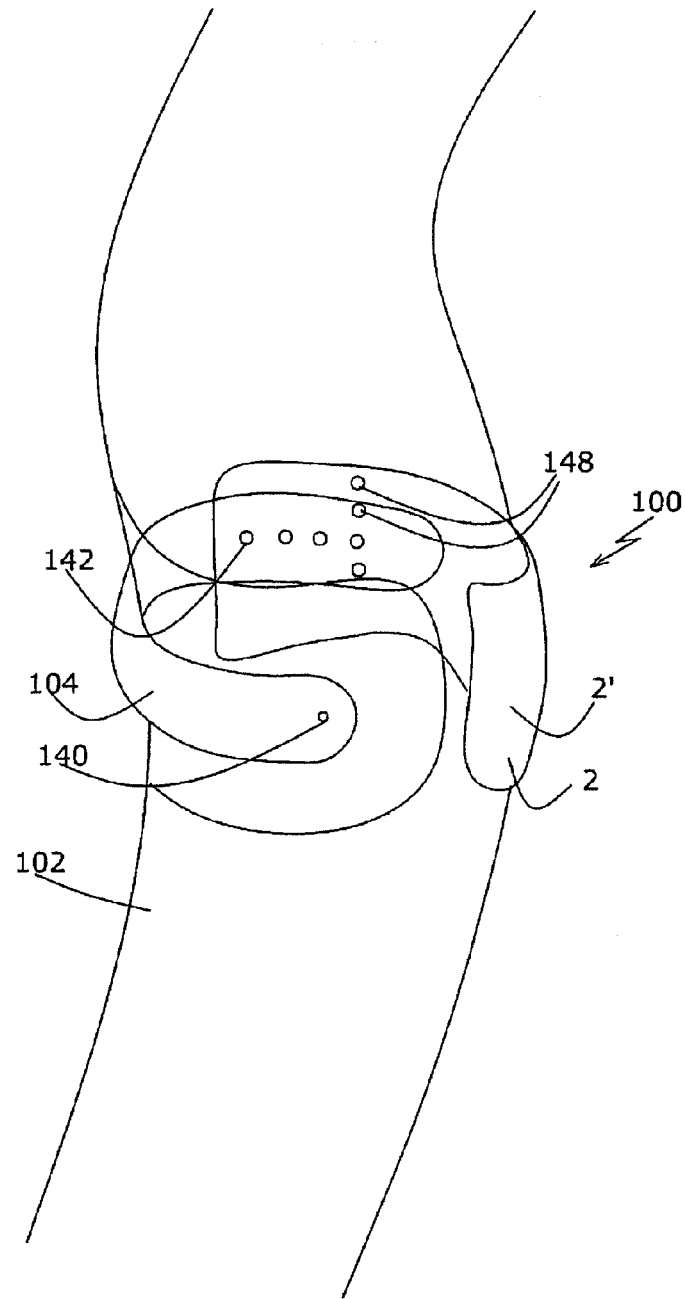
FIG. 20 is a schematic illustration of another preferred embodiment of the neuroprosthetic device of the present invention that allows for circumferential and/or longitudinal adjustment of the device with respect to the limb segment.

FIG. 20 is a schematic illustration of another preferred embodiment of the neuroprosthetic device of the present invention, based upon neuroprosthetic device 100 of FIG. 15, and allowing for positional adjustment of shell 2' with respect to body limb segment 102. The positional adjustment is predominantly in two directions: longitudinal adjustment along the length of limb segment 102, and circumferential adjustment around limb segment 102. To this end, horse-shoe-shaped cantilever 104 is fitted with a circumferential adjustment slot 140 or circumferential attachment points 142. Shell 2' is similarly fitted with longitudinal adjustment slot (not shown) or longitudinal attachment points 148. Connection joint 106 connects cantilever 104 to shell 2' and shell 2, respectively, via the above-described attachment points and adjustment slots. At an initial device set-up session the relative position of shells 2, 2' may be adjusted for an individual patient.

Figure 21:
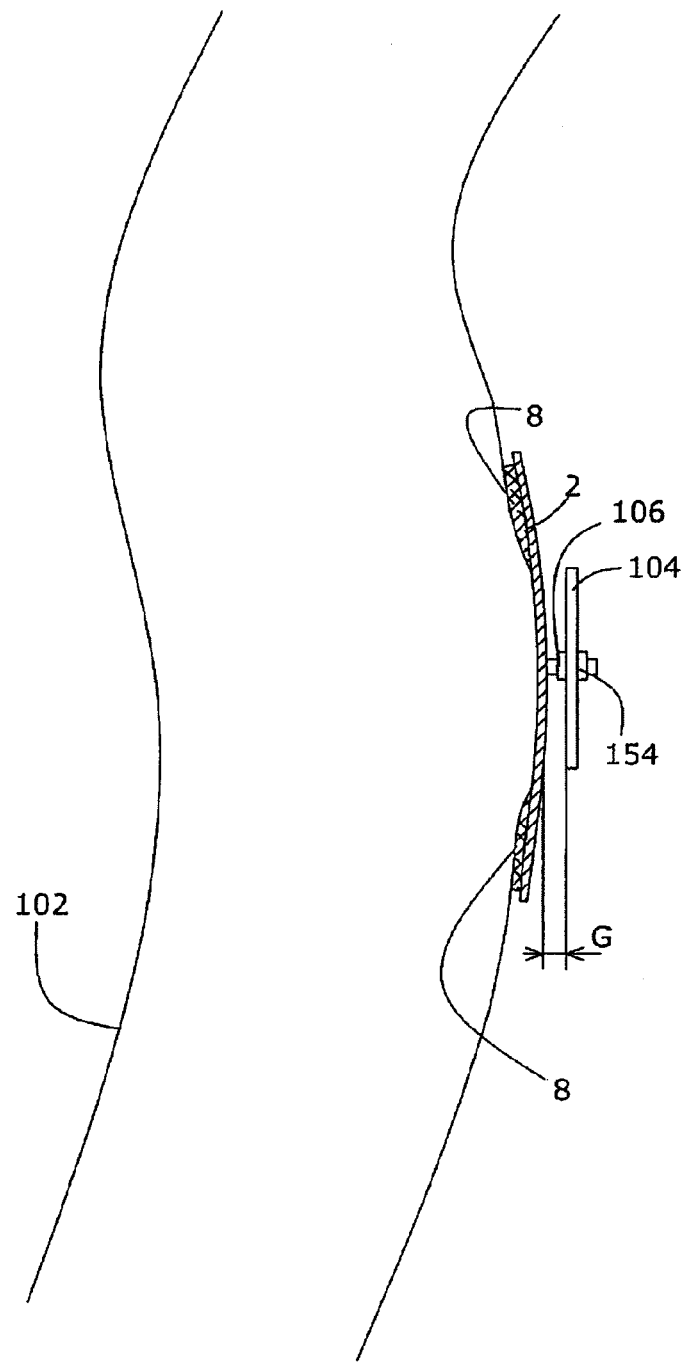
FIG. 21 is a schematic illustration of another preferred embodiment of the present invention that allows for radial adjustment of the device with respect to the limb segment.

Another preferred embodiment of the present invention, shown schematically in FIG. 21, allows for radial positional adjustment of the neuroprosthetic device with respect to body limb segment 102. The gap G between cantilever 104 and shell 2 is adjustable by means of cantilever screw assembly 154. A larger gap G provides shell 2 with a wider range of rotation for self-adjustment of orientation with respect to the surface of limb segment 102. As gap G is narrowed by means of cantilever screw assembly 154, shell 2 and hence, surface electrodes 8 fit more snugly against the surface of body limb segment 102.

Neuroprosthetic device 100 of the present invention is preferably of modular design (see FIG. 15, by way of example), such that shells 2, 2' can be made in different sizes and shapes, yet are fully connectable to cantilever 104 by means of connection joint 106. Hence, even custom-sized shell 2a, shown in FIG. 22, is mountable on neuroprosthetic device 100. This feature provides flexibility in selecting the shell size and shape for individual patients coupled with compatibility with standard cantilever 104.

Neuroprosthetic device 100 may be adapted to a left or right limb segment. To this end, it is usually sufficient to rotate cantilever 104 by 180° with respect to connection joint 106.

The neuroprosthesis surface electrodes 8 may be preset in specific positions or at specific orientations within the shell or may be of specific size or type. At the device fitting session, shells bearing optimal electrode type, size, position, and orientation may be selected for the neuroprosthesis of the patient, and the selected shells fitted to the device.

Although cantilever 104 of FIG. 15 typically applies a force to the approximate center of shells 2, 2', additional interactions can improve the contact between the shells 2, 2' and the surface of limb segment 102 for an individual patient. As shown schematically in FIG. 15, by way of example, a localized, positive displacement between the cantilever and shell may be provided by a displacement mechanism 170, which preferably includes an adjustment screw. Local elastic deformation of the semi-rigid shell 2 may be provided by this adjustment screws. Alternative displacement/deformation mechanisms, including a spring link (not shown) interposed between the cantilever and shell, will be readily apparent to those skilled in the art.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surface neuroprosthetic device for functional electrical stimulation (FES), the device comprising:

a surface neuroprosthesis including:

(a) at least a first exoskeletal shell and a second exoskeletal shell, each including an outer member having an at least semi-rigid material, said shells being configured to at least partly envelop a limb portion of a user;

(b) at least one electrical stimulation electrode associated with, and supported by, at least said first exoskeletal shell, said first exoskeletal shell substantially covering and surrounding said at least one electrical stimulation electrode, and (c) a linear closure mechanism, connecting said shells, said mechanism designed to draw said shells together in a substantially linear fashion, such that when said limb portion is disposed between said shells, said closure mechanism applies to said electrical stimulation electrode, via said shells, a compressive force, so as to maintain a continuous electrical contract between said at least one electrode and a skin surface of said limb portion, thereby providing controlled, useful muscular function to said limb.

2. The surface neuroprosthetic device of claim 1, said closure mechanism for constraining movement of said exoskeleton shell and said at least one electrode to a substantially linear motion in a direction radial to a long axis of said limb while donning said neuroprosthesis, so as to prevent shear deformation of a soft tissue of said limb.

3. The surface neuroprosthetic device of claim 1, wherein said first exoskeletal shell is designed to generally conform to said limb portion of said user.

4. The surface neuroprosthetic device of claim 1, wherein said shells are designed to substantially conform to said limb portion of said user.

5. The surface neuroprosthetic device of claim 1, further comprising a retaining mechanism for retaining said shells in a selected position of translation.

6. The surface neuroprosthetic device of claim 5, wherein said retaining mechanism includes a pawl and ratchet arrangement, said pawl being associated with one of said shells and said ratchet being associated with another of said shells.

7. The surface neuroprosthetic device of claim 6, wherein said ratchet is an integral part of a flexible strip operatively connected to a slider.

8. The surface neuroprosthetic device of claim 6, wherein said substantially linear movement is effected by a pin riding in an inclined slot in a slider connected to one of said shells and kinematically connected to a trigger member of said pawl, whereby a sliding movement of said trigger member causes said slider to move in a direction perpendicular to said sliding movement.

9. The surface neuroprosthetic device of claim 1, further comprising at least one tension spring connected at one end to a first of said shells and at an opposite end to a second of said shells so as to produce tension between said shells, said tension urging said shells into a normally-closed position.

10. The surface neuroprosthetic device of claim 1, further comprising at least one compression spring connected at one end to a first of said shells and at an opposite end to a second of said shells so as to produce tension between said shells, said tension urging said shells into a normally-open position.

11. The surface neuroprosthetic device of claim 1, wherein an opening movement and a closing movement of said shells are effected by an interaction of a first pair of inclined planes fixedly attached to a first of said shells with a second pair of inclined planes fixedly attached to a second of said shells, wherein said second pair of inclined planes is biased by a force of a tension spring to facilitate said closing movement of said shells.

12. The surface neuroprosthetic device of claim 1, the device being designed and configured to be donned by said user using a single hand.

13. The surface neuroprosthetic device of claim 1, further comprising at least one cushion, each said at least one cushion operatively connected to said first shell and disposed between said first shell and said at least one electrical stimulation electrode.

14. The surface neuroprosthetic device of claim 1, wherein said substantially linear movement of said shells allows for maintaining a natural limb shape of said limb portion.

15. The surface neuroprosthetic device of claim 1, wherein said closure mechanism includes a cantilever.

16. The surface neuroprosthetic device of claim 15, wherein said cantilever is connected to each of said shells at a single connection joint.

17. The surface neuroprosthetic device of claim 15, wherein said cantilever is connected to said shells such that said pressure delivered to said at least one electrode is a substantially even pressure.

18. The surface neuroprosthetic device of claim 15, further comprising a spring biasing mechanism, operatively connected to a shell of said shells and to said cantilever, said spring mechanism for biasing a pressure exerted on said skin surface of said limb portion.

19. The surface neuroprosthetic device of claim 18, wherein said at least one electrical stimulation electrode includes a first electrode and a second electrode, and wherein said spring mechanism is for biasing a pressure exerted on said first electrode with respect to said second electrode.

20. The surface neuroprosthetic device of claim 15, further comprising a locking mechanism operatively connected to a shell of said shells and to said cantilever, said locking mechanism for locking a connection joint in a fixed position.

21. The surface neuroprosthetic device of claim 20, wherein said locking mechanism includes an adjustable screw assembly for adjustably locking said connection joint in said fixed position.

22. The surface neuroprosthetic device of claim 15, wherein said cantilever includes circumferential adjustment means for circumferentially fitting the device to said lint portion of said user.

23. The surface neuroprosthetic device of claim 15, wherein said cantilever includes longitudinal adjustment means for longitudinally fitting the device to said limb portion of said user.

24. The surface neuroprosthetic device of claim 15, wherein said cantilever includes radial adjustment means for radially adjusting the device to said limb portion of said user, so as to adjust a gap width between said cantilever and a shell of said shell.

25. The surface neuroprosthetic device of claim 15, wherein said cantilever includes a displacement mechanism between said cantilever and a shell of said shells for providing a localized, positive deformation of said shell, enabling control of local pressure applied to said limb portion.

26. The surface neuroprosthetic device of claim 1, wherein at least one shell of said shells further includes a second material having a greater flexibility with respect to said at least semi-rigid material, said second material for enabling local, controlled flexibility of said shell.

27. The surface neuroprosthetic device of claim 26, wherein said second material is an elastomer.

28. A method of donning and doffing a surface neuroprosthetic device for functional electrical stimulation (FES) of a limb, the method comprising the steps of:
   (a) providing a surface neuroprosthetic device including:
      (i) at least a first exoskeletal shell and a second exoskeletal shell, each including a member having an at least semi-rigid material, said shells being configured to at least partly envelop a limb portion of a user;
      (ii) at least one electrical stimulation electrode associated with, and supported and surrounded by, at least said first exoskeletal shell, and
      (iii) a closure mechanism, connecting said shells;
   (b) disposing said device around said limb portion, and
   (c) moving said shells in a substantially linear movement with respect to each other, using said closure mechanism, to effect a closing of said device around said limb portion, such that said shells envelop at least a part of said limb portion,
   wherein said closure mechanism applies to said at least one electrical stimulation electrode, via said shells, a compressive force,
   such that upon powering of said device, a continuous electrical contract is delivered between said electrode and a skin surface of said limb portion, so as to provide controlled, useful muscular function to the limb.

29. The method of claim 28, wherein said closing is performed with a single hand.

30. The method of claim 28, wherein said closing is performed with a single hand by said user.

31. The method of claim 28, further comprising the step of:
   (d) donning said device with a single hand.

32. The method of claim 28, father comprising the step of:
   (d) doffing said device with a single hand.

33. The method of claim 28, further comprising the step of:
   (d) donning said device, by said user, in an accurate and repeatable manner.

34. The method of claim 28, further comprising the step of:
   (d) donning said device while maintaining a natural shape of said limb portion.

35. The method of claim 28, wherein said first exoskeletal shell substantially covers said at least one electrical stimulation electrode.

* * * * *